United States Patent
Wrench et al.

(10) Patent No.: US 9,921,193 B2
(45) Date of Patent: Mar. 20, 2018

(54) BOTTLE PRESSURIZATION DELIVERY SYSTEM

(71) Applicant: Bio-Rad Laboratories, Inc., Hercules, CA (US)

(72) Inventors: Nathan Wrench, Swaffham Prior (GB); William Mainwaring-Burton, Cambridge (GB); Chris Butcher, Pleasant Hill, CA (US); Nick Harrison, Oakington (GB)

(73) Assignee: Bio-Rad Laboratories, Inc., Hercules, CA (US)

( * ) Notice: Subject to any disclaimer, the term of this patent is extended or adjusted under 35 U.S.C. 154(b) by 301 days.

(21) Appl. No.: 14/213,001

(22) Filed: Mar. 14, 2014

(65) Prior Publication Data
US 2014/0261868 A1    Sep. 18, 2014

Related U.S. Application Data

(60) Provisional application No. 61/785,000, filed on Mar. 14, 2013.

(51) Int. Cl.
*G01N 30/32* (2006.01)
*G01N 30/16* (2006.01)
(Continued)

(52) U.S. Cl.
CPC ........... *G01N 30/32* (2013.01); *B67D 7/0255* (2013.01); *G01N 30/16* (2013.01); *G01N 30/22* (2013.01);
(Continued)

(58) Field of Classification Search
CPC .... B01D 19/0031; B01D 29/62; B01D 29/72; G01N 1/34; G01N 2001/4088;
(Continued)

(56) References Cited

U.S. PATENT DOCUMENTS 4,994,180 A    2/1991  Sims et al.
5,046,332 A *  9/1991  Herrmann ............. A23L 3/3418
                                                 62/388
(Continued)

FOREIGN PATENT DOCUMENTS

CN    101484782 A    7/2009
EP      1097899 A1    5/2001
(Continued)

OTHER PUBLICATIONS

International Search Report an Written Opinion dated Jul. 25, 2014, from PCT Application No. PCT/US14/28981 (15 pages).
(Continued)

*Primary Examiner* — Lyle Alexander
*Assistant Examiner* — Bryan Kilpatrick
(74) *Attorney, Agent, or Firm* — Kilpatrick Townsend & Stockton LLP (57) ABSTRACT

A container assembly for use with a high-pressure liquid chromatography (HPLC) instrument is disclosed, in which the container assembly, when coupled to a source of pressurized gas, provides fluid medium to the HPLC instrument at positive pressure. The container assembly has an external exterior container shell, an internal fluid container for holding fluid medium, an interstitial volume between the external exterior container shell and the internal fluid container, a port for fluidly connecting the volume to a pressurized gas source, and a port for fluidly connecting the internal fluid container to the HPLC instrument. As a pressurized gas in the interstitial volume increases, fluid medium flows out of the port connected to the internal fluid bag and container assembly at a positive pressure. A system incorporating the container assembly, and method of use of the same, are also disclosed.

11 Claims, 8 Drawing Sheets

(51) Int. Cl.
*G01N 30/22* (2006.01)
*G01N 30/88* (2006.01)
*B67D 7/02* (2010.01)

(52) U.S. Cl.
CPC ..... *G01N 30/88* (2013.01); *G01N 2030/8881* (2013.01); *Y10T 137/9029* (2015.04)

(58) Field of Classification Search
CPC ........... G01N 2030/8881; G01N 30/32; G01N 30/88; Y10T 137/9029
See application file for complete search history.

(56) References Cited

U.S. PATENT DOCUMENTS

| | | | | |
|---|---|---|---|---|
| 5,242,586 | A | | 9/1993 | Ransohoff |
| 5,352,585 | A | * | 10/1994 | Binder ................. G01N 30/461 422/70 |
| 5,416,023 | A | * | 5/1995 | Binder ................. G01N 30/461 210/198.2 |
| 6,491,816 | B2 | | 12/2002 | Petro |
| 7,204,679 | B2 | * | 4/2007 | Wheeler ................. B24B 37/04 417/390 |
| 8,387,817 | B1 | | 3/2013 | Zelechonok |
| 2006/0145814 | A1 | * | 7/2006 | Son ....................... F25D 29/005 340/10.1 |
| 2010/0270296 | A1 | | 10/2010 | Rauleder et al. |
| 2011/0138877 | A1 | * | 6/2011 | McCauley ........... B01D 53/053 73/23.37 |

FOREIGN PATENT DOCUMENTS

| | | |
|---|---|---|
| TW | 442429 B | 6/2001 |
| WO | 2007146892 A2 | 12/2007 |
| WO | 2012/040574 A1 | 3/2012 |
| WO | 2012/058516 A1 | 5/2012 |

OTHER PUBLICATIONS

EP14767684, "Extended European Search Report", dated Oct. 13, 2016, 9 pages.
English translation of Office Action dated Mar. 8, 2017 in CN Patent Application 201480015053.9. 14 pages.
Examination Report No. 1 dated Sep. 18, 2017 in AU Patent Application No. 2014236334. 3 pages.

* cited by examiner

BOTTLE PRESSURIZATION DELIVERY SYSTEM

CROSS-REFERENCE TO RELATED APPLICATION

This application claims the benefit of priority to U.S. Provisional Patent Application No. 61/785,000 filed on Mar. 14, 2013, the content of which is hereby incorporated by reference.

BACKGROUND OF THE INVENTION

The present invention resides in the field of high-pressure, or high-performance, liquid chromatography (HPLC) assays, particularly for the delivery of reagents, diluents, solvents, and other fluids an HPLC instrument and apparatus system. More specifically, the present invention is directed to a fluid handling system for the delivery of solvent fluids with positive pressure to an HPLC instrument.

HPLC is a chromatographic technique used to separate a mixture of compounds in analytical chemistry and biochemistry with the purpose of identifying, quantifying or purifying the individual components of the mixture. Generally, HPLC relies on pumps to pass a pressurized liquid and a sample mixture through a column filled with a sorbent, leading to the separation of the sample components. The active component of the column, the sorbent, is typically a granular material made of solid particles. The components of the sample mixture are separated from each other due to their different degrees of interaction with the sorbent particles. The pressurized liquid is typically a mixture of solvents (e.g. water, acetonitrile, methanol) and is referred to as "mobile phase". In addition to the composition and temperature of the mobile phase, the fluid pressure of the mobile phase plays a major role in the separation process by influencing the interactions taking place between sample components and sorbent. These interactions are physical in nature, such as hydrophobic (dispersive), dipole-dipole and ionic, most often a combination thereof.

HPLC instruments and techniques have become increasingly sophisticated and complex, allowing for the analysis of multiple portions of a sample, utilizing a variety of different solvent fluids or analyzing a variety of samples with the same or different solvents. Such systems require fluid distribution systems capable of allocating precise amounts of solvents at specific pressures, for extended durations of time, and the ability to switch from one solvent to another.

HPLC systems known in the field often require that the solvent fluids to be used by the instruments be elevated, so as to take advantage of gravity, drawing down the solvent fluids into the instrument, and thus priming the fluid lines of the HPLC instrument.

In view of the above, there remains a need to provide solvents to HPLC instrumentation without the disadvantages noted above and known in the field.

BRIEF SUMMARY OF THE INVENTION

Embodiments of the present disclosure are directed to a pressurized system for the delivery of fluid mediums, such as solvent fluids, into an HPLC instrument, and to modules within an HPLC instrument such as a pump set, a separation module, or a dilution module. An array of bottles (also referred to as "reagent boxes" or "container assemblies") each contain an enclosed bag or pouch, within which solutions of solvents, reagents, buffers, diluents, and/or other fluid mediums are contained. The interstitial volume of space between the bag the inside of the bottles is then pressurized with a gas, such as air. The increased gas pressure exerts force on the exterior of the bag, encouraging the egress of fluid medium, such as solvent fluid, from the enclosed bag through fluid connectors. The fluid connectors lead into the HPLC instrument and thus the present disclosure provides solvent fluids to an HPLC instrument and system at a positive pressure, relative to ambient conditions.

Some embodiments of the present disclosure include shut-off valves on the fluid connectors of the bottles prevent fluid egress when the bottle is outside of or not properly coupled to an HPLC instrument. Shut-off connectors are also used on the HPLC instrument in order to prevent the aspiration of air by pumps if a bottle is not connected. Each bottle position on the HPLC instrument has an individual valve for pressurization and depressurization, which is fed from a centralized reservoir and releases to ambient atmosphere. In the case of a bag failure causing the volume of space in the bottle to fill with pressurized fluid, the valves vent away from the electronics within the HPLC instrument, into drip trays. The bottles may be made of metal, plastic, reinforced materials, or another appropriate rigid or semi-rigid materials, in order to generally maintain the form of the bottles when under pressure. In aspects, the structural walls of such bottle can restorably flex, expanding to a degree when under pressure and returning to a base, unexpanded state when not under pressure. A bottle may reside within an additional external housing, to assist in maintaining the form of and reinforce the bottles when under pressure.

Further embodiments of the present disclosure allow for providing fluid at a positive pressure to an instrument without the need for additional elevation in order to prime the system. The positive pressure also facilitates the use of a forward pressure degassing system, which requires no pump. The combination of positive pressure in the reagent consumable, coupled with the debubblers in the bulk fluids module of the present system, enables the consumables to be connected to the system easily without injecting bubbles of air into the fluidic system.

Some embodiments of the present disclosure comprise a container assembly for holding an fluid medium, the container assembly comprising: an external container having a first port and a second port, the external container defining a volume fluidly connected to the first port; and an internal container contained within the external container and being fluidly sealed from the volume, the internal container holding an fluid medium and being fluidly connected to the second port by way of a valve.

Further embodiments of the present disclosure comprise a method of handling fluid medium within an instrument, comprising: holding an internal container within an external container, the external container defining a volume fluidly sealed from the internal container; holding an fluid medium within the internal container; coupling a first port to the external container to a pressurization system of the instrument compressing the internal container by filling the volume with pressurized gas through the first port; coupling a second port to the internal container to a system of an instrument; and delivering the fluid medium from within the internal container at a positive pressure to the instrument through the second port.

Some embodiments of the present disclosure comprise a system for the handling of an fluid medium in an instrument, comprising: a gas intake and pressurization apparatus; a plurality of container assemblies, with each container assembly comprising an external container having a first port and a second port, each external container defining the first volume fluidly connected to the first port, and an internal container defining the second volume contained within the external container and being fluidly sealed from the first volume, with each first volume being fluidly connected to the gas intake and pressurization apparatus, and with each second volume holding an fluid medium; and an instrument fluidly connected to each container assembly second volume, such that fluid medium from each container assembly can enter the instrument.

It is to be noted that while the present disclosure is generally directed to HPLC instrumentation and chemistries, the pressurized system for the delivery of fluid medium can be used for any appropriately designed chemistry or biochemistry instrument that requires the pressurized delivery of reagents, buffers, diluents, solvents, or other fluid mediums.

BRIEF DESCRIPTION OF THE DRAWINGS

Illustrative aspects are described in detail below with reference to the following drawing figures.

DETAILED DESCRIPTION OF THE INVENTION

The present disclosure is directed to a pressurized system for the delivery of fluid mediums into an HPLC instrument and system, wherein a bottle, or reagent box, is used to store and supply solvents. The reagent box is designed for simple and efficient loading and locking into an HPLC instrument, minimizing the time and work required to replenish reagents on an HPLC instrument. The reagent box may also improve the shelf life of the solvents stored within the reagent box.

As used herein, the term "fluid medium" can refer to any one of a reagent solution, a buffer solution, a solvent, a diluent, a sample fluid (such as blood, urine, or other biological fluids), and/or other fluids. Such fluid mediums can be those that are used, or known in the art to be used, as part of a mobile phase in HPLC instrumentation. In alternative embodiments, fluid mediums, and the pressurized delivery of fluid mediums, can be applied toward general life science or diagnostic research fluidic instrumentation, such as instrumentation for ion exchange chromatography, protein purification, solid phase extraction, liquid-liquid extraction, distillation, fractional distillation, fluid separation, magnetic separation, stripping, membrane or mesh filtration, flocculation, elutriation, leaching, or other such instrumentation. In some aspects, the fluid medium can be an HPLC solvent, i.e. a fluid specific for use with HPLC instrumentation. In further aspects, the fluid medium can be fluids used in separation techniques, filtration techniques, extraction techniques, purification techniques, distillation techniques, flocculation techniques, elution techniques, leaching techniques, or the like. Exemplary fluid mediums include, but are not limited to, water, acetic acid, acetone, acetonitrile, carbon disulphide, carbon tetrachloride, chlorobenzene, chloroform, cyclohexane, cyclopentane, dichloromethane, 1,2-dichloroethane, diethyl ether, dimethylformamide, dimethylsulfoxide, dioxan, ethanol, ethyl acetate, fluoroalkanes, heptane, hexane, methanol, methyl ethyl ketone, m-xylene, n-butyl acetate, n-butyl ether, nitromethane, n-methyl pyrollidone, pentane, petroleum ether, 1-propanol, 2-propanol, pyridine, tetrahydrofuran, toluene, triethylamine, 2,2,4-trimethylpentane, and combinations, mixtures, and variations thereof.

The use of the reagent box further allows for easy identification of the reagent fluid contained within the bottle. This can be accomplished by color-coding the reagent box itself. In addition or alternatively, the reagent box can be barcoded, QR-coded, or otherwise labeled with identifying data. Further, the identity of an individual reagent box can be stored in a computerized database linked to a fluid instrument system, such as a HPLC system, so as to keep track of how much fluid medium has been dispensed from any given reagent box. Information regarding the content and/or volume of fluid medium remaining in a bottle can be disclosed to a user of an instrument by use of indicator lights. In aspects, such indicator lights can indicate that the amount of fluid medium remaining in a bottle is sufficient, that the amount of fluid medium remaining in a bottle is of concern, and/or that there is no fluid medium remaining in the bottle. Information regarding the content and/or volume of fluid medium remaining in a bottle, and also information regarding the number of tests run on an instrument with the bottles, can be stored, displayed, and/or manipulated on a computer system coupled with the fluid instrument system. A barcode reader or a QR-code reader may also be connected to a computer system coupled with a fluid instrument system and provide for data entry of the information barcoded or QR-coded on a reagent box.

In further aspects, a reagent box can include a non-transitory computer-readable memory component that can store information regarding the volume of fluid medium held in the reagent box. The non-transitory computer-readable memory can be updatable, such that as fluid medium decreases in the reagent box, the amount of remaining fluid medium in the box is updated to store information regarding the actual amount of fluid medium in the reagent box. Accordingly, if the reagent box is transferred from one fluid instrument system to a subsequent fluid instrument system, the subsequent fluid instrument system can obtain information regarding the amount of fluid medium in the reagent box from the non-transitory computer-readable memory component. In some aspects, the non-transitory computer-readable memory component can be updated using RF transmission from the fluid instrument system, for example, using RFID. In other aspects, the non-transitory computer-readable memory component can be electronically coupled to a fluid instrument system, and thereby updated, when the reagent box is mechanically coupled to the fluid instrument system.

The present disclosure also provides for the ability to change the buffer and reagents as the HPLC instrument is operating, i.e. on-the-fly, simply by swapping out reagent boxes. This can allow for a longer operation time of a fluidic instrument consuming fluid mediums, since reagent, solvent, diluent, and buffer fluids can be replenished as needed. When a reagent box is swapped out, air may fill the space between the fluid connections on the reagent box and the HPLC instrument. However, a debubbler, such as a porous membrane allows gas to pass through but not liquid, positioned on the HPLC side of the fluid connection can be used to prevent air bubbles or pockets from entering the fluidic system.

Many embodiments also provide for the advantage that the container assemblies can be loaded onto an HPLC instrument horizontally, in a cantilever orientation. This allows for an HPLC instrument configuration and design which does not require fluid mediums or other fluids to be at an elevated position on an instrument. Such embodiments can provide for the delivery of fluid mediums at a positive pressure, thus removing the need to use gravity to drawn down fluid medium fluids into the fluid lines of an instrument, e.g. in order to prime the lines of an instrument.

While the bottles holding fluids are referred to herein as "reagent" boxes, it is to be understood that the fluid contents of a reagent box can include reagents, diluents, buffers, water, solvents, or any other appropriate fluid medium.

Figure 1:
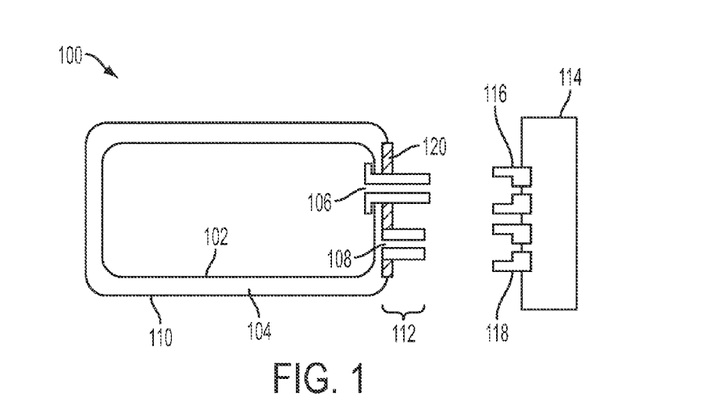
FIG. 1 is an architectural schematic of the reagent box, according to some embodiments.

FIG. 1 is an architectural schematic of the reagent box and its component parts 100. The reagent box shell 110 of the reagent box can be made of metal, plastic, polymer, metal-reinforced polymer, or other appropriate materials that can both protect the contents in the interior of the reagent box and withstand stresses related to handling and storage. Accordingly, in aspects, the reagent box can be rigid or semi-rigid, particularly when considered relative to a fluid bag 102. In some aspects, the reagent box can be referred to as an external container. The fluid bag 102 can be made of a flexible material that holds a fluid medium, and of a size that fits within the interior of the reagent box shell 110. In aspects, the flexible material can be an elastic, an inelastic, or a semi-elastic polymer material. In further aspects, the fluid bag 102 can be referred to as an internal container. The interstitial volume 104 (alternatively referred to as a first volume), being the space in between the interior surface of the reagent box shell 110 and the exterior surface of the fluid bag 102, can be filled with a gas. A gas, such as air, can be pumped into interstitial volume 104 through a gas interface port 108. As gas fills interstitial volume 104 of a sealed reagent box, the pressure from the gas entering the volume of the reagent box can push fluid medium inside the fluid bag 102 out through any egress that exists in the reagent box, primarily through the fluid interface port 106. In some aspects, the volume of the fluid bag 102 can be referred to as second volume. A reagent box shell 110 can be sealed with a reagent box cap 114 that fits over the open end region 112 of the reagent box shell 110. The reagent box cap 114 further includes a fluid interface connector 116 which can couple to the fluid interface port 106, and a gas interface connector 118 which can couple to the gas interface port 108. The gas interface connector 118 when connected to the gas interface port 108 forms a pathway that allows for gas to be pumped into the interstitial volume 104 of the reagent box shell 110. The fluid interface connector 116 when connected to the fluid interface port 106 forms a pathway that allows for fluid to exit the fluid bag 102, which in operation is designed to be in response to the increased gas pressure of the interstitial volume 104 pushing on the exterior surface of the fluid bag 102. An interface plate 120 surrounds and secures a cross-section of the fluid interface connector 116 and gas interface connector 118 to the fluid bag 102.

Figure 2:
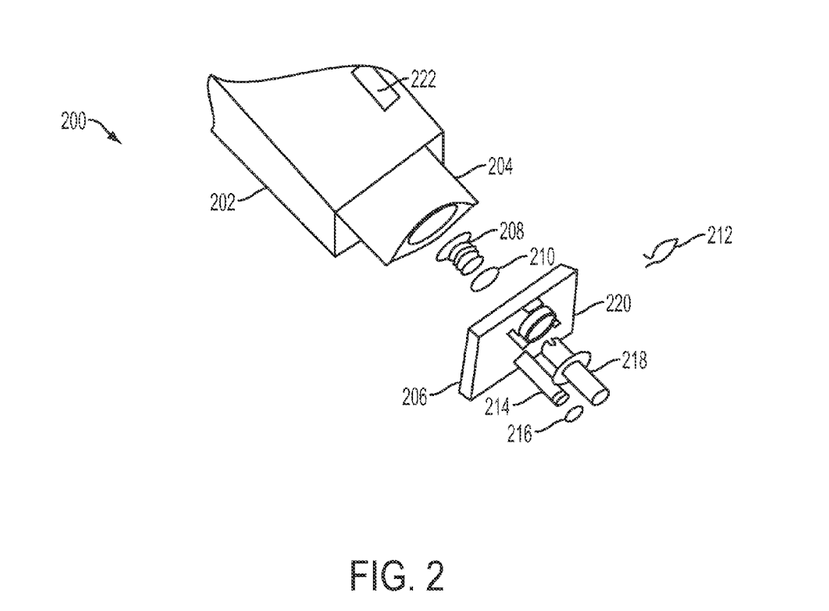
FIG. 2 is an exploded-view illustration of the reagent box and its component parts, according to some embodiments.

FIG. 2 is an exploded-view illustration of the reagent box 200. The reagent box shell 202, as noted above, can be made of materials that can both protect the contents in the interior of the reagent box and hold up to external stresses of handling and storage. Further, the reagent box shell 202 can be molded, contoured, or constructed in order to fit and interface with an HPLC instrument, or other fluidic instrument, as well as in order to be easily handled by a user. The fluid bag 204, which can be made of any appropriate flexible material capable of holding fluid, can be shaped and/or contoured to fit within the reagent box shell 202. The fluid bag 204 can be made of materials that are biologically inert and chemically inert, capable of withstanding the range of solvents, acids, bases, and other liquids that can have corrosive characteristics. Further, the fluid bag 204 can be shaped, tapered, and/or contoured to efficiently allow solvents to egress the fluid bag 204 through the fluid interface port 208 (alternatively referred to as a nozzle) when the exterior surface of the fluid bag 204 is under pressure. The shaping or tapering of the fluid bag 204 can mitigate against solvents being pushed to the sides, corners, or back of the fluid bag 204 when under pressure, by channeling or directing the held fluid medium toward the exit of the fluid bag 204 at the fluid interface port 208. The fluid medium accordingly exits the fluid bag 204 at a positive pressure. This can help to maximize the use of any fluid medium, reagent, buffer, diluent, or other solvent in a fluid bag 204 and minimize the waste of any unused solvents. As shown, the fluid bag 204 is bordered by flat edging that causes the fluid bag 204 to substantively flatten under pressure.

The reagent box cap 206 can be made of the same material or a different material as the reagent box shell 202. The reagent box cap 206, when mechanically coupled with the reagent box shell 202, provides for a sealed (i.e. airtight) interstitial volume such that the gas in the volume between the interior surface of the reagent box shell 202 and the exterior surface of the fluid bag 204 will increase in pressure as more gas is pumped into volume. The seal between the coupled reagent box shell 202 and reagent box cap 206 should not break as gas pressure in the interstitial volume increases. The reagent box cap 206 further includes a gas interface port 214 for providing gas to the interstitial volume. A gas interface port O-ring 216 can be used to help secure the gas interface port 214 to a mechanical structure, such as a pipe or tube, used to channel gas into the reagent box. A fluid interface port O-ring 210 can be used to help secure the fluid interface port 208 as it mechanically couples with the reagent box cap 206, the reagent cap fluid port 220, and fluid interface connector 218. An interface connector latch 212 can be used to further secure the connection between the fluid interface connector 218 as it is seated within the reagent cap fluid port 220 and/or the fluid interface port 208. The fluid interface port 208 can be threaded or otherwise molded to mechanically couple with the reagent cap fluid port 220, or to guide and control the flow of fluids that egress from the fluid bag 204.

In alternative embodiments, the reagent box or container assembly may not be built from a severable reagent box cap and reagent box shell. The reagent box can be constructed from parts that are permanently sealed together using methods known in the art. Alternatively, ports may be formed in a single body shell using methods known in the art, through which a fluid bag may be inserted and into which interface connections can be installed.

The reagent box shell 202 can further include a label region 222 on which a barcode, QR-code, or other identifying marking can be printed or affixed. A label region 222 can be on any part of the external surface of the reagent box shell 202, as appropriate for handling and identifying the reagent box individually or coupled with an HPLC instrument.

Figure 3:
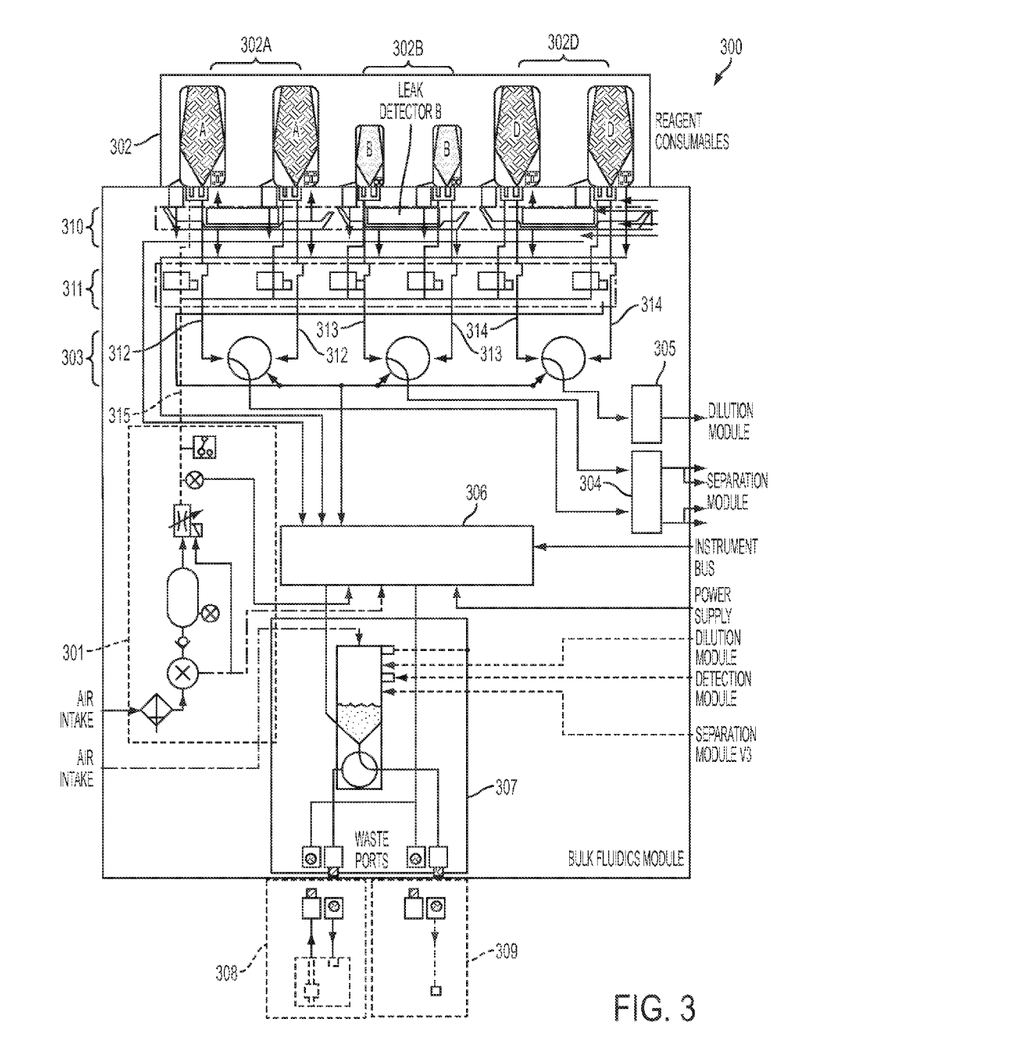
FIG. 3 depicts a design flowchart illustrating the interaction and connections between aspects of the bulk fluidics module, according to some embodiments.

FIG. 3 is a design flowchart illustrating the interaction and connections between all aspects of the bulk fluidics module 300. Air (or in alternative embodiments, a gas from a controlled gas supply) is drawn into the bulk fluidics module 300 through the consumable pressurization system 301. The consumable pressurization system 301 pressurizes the air and is sent to the reagent consumable region 302 through pressurized gas channel 315, which can be a hollow piping, tubing, or the like. Air pressure sensors within the consumable pressurization region 301 monitor the air pressure, sending that information to the control electronics 306. Based on that pressure data, the control electronics 306 send instructions to controllers within the consumable pressurization region 301 to regulate the air pressure therein. Within the reagent consumable region 302 there are a plurality of reagent boxes, 302a, 302b, and 302d, which can contain fluids such as solvents, reagents, buffer, or diluent. The pressurized air delivered to the reagent consumable region 302 through the pressurized gas channel 315 is more specifically delivered into the gas receiving structure of each reagent box. As pressurized gas is pumped into the interstitial volume of a reagent box, fluid medium is pushed (at a positive pressure) out of the fluid bag inside the reagent box, out through the leak detection region 310 and into the consumable decompression region 311. The fluid medium from each reagent box is pushed through a fluid channel dedicated that fluid medium. For example, as illustrated in FIG. 3, fluid channel 312 is dedicated to fluid medium from reagent box 302a, fluid channel 313 is dedicated to fluid medium from reagent box 302b, and fluid channel 314 is dedicated to fluid medium from reagent box 302d. In embodiments, there may be more than one reagent box connected to a fluid channel, such that multiple reagent boxes with the same fluid, i.e. the same reagent, the same buffer, etc., can be provided to a single fluid channel system.

The leak detection region 310 is designed to detect leaks from the reagent consumable region 302. Leaks detected from the reagent consumable region 302 will be sensed by sensors in the leak detection region 310, where the sensors can be thermal-based sensors, voltage-based sensors, current-based sensors, or the like. Upon detection of a leak, the control electronics 306 can operate to trigger a warning indicator for a user, reduce or shut off pressurization of the reagent boxes, close valves, or execute other actions to minimize and/or stop further leakage.

The consumable decompression region 311 includes valves that take in the fluid medium expelled from the related reagent boxes, and regulates the pressure of each fluid medium before further delivering said fluid mediums to the next stages of an HPLC instrument. From the consumable decompression region 311, the fluid medium from reagent boxes which are reagents and buffers, such as 302a and 302b, are further directed to a buffer conditioner 304, and then further directed out of the bulk fluidics module 300, such as to a separation module of the HPLC instrument. Similarly, the fluid medium from reagent boxes which are diluents 302d are further directed from the consumable decompression region 311 to a diluent conditioner 305, and then further directed out of the bulk fluidics module 300, such as to a dilution module of the HPLC instrument.

Following processing in the separation module and dilution module of the HPLC instrument, waste fluids from the HPLC instrument (i.e. solvents run through a sorbent column) are returned to the bulk fluidics module 300, specifically to the waste combiner subassembly 307. The waste fluids, once combined, can be further shunted to a waste container 308 as a separate section of the HPLC instrument and/or a waste pipe 309 leading out of the HPLC instrument entirely.

Figure 4:
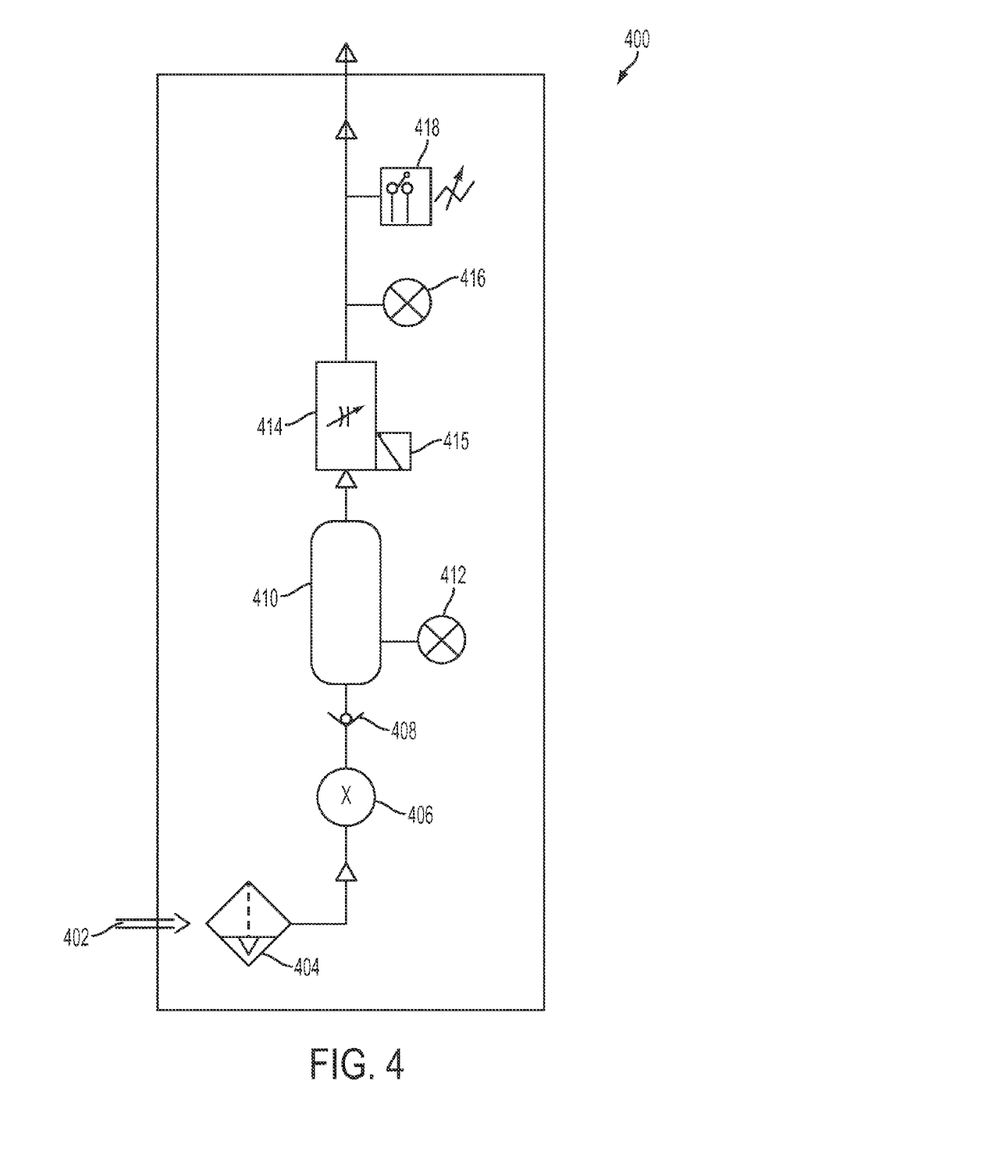
FIG. 4 is a detail schematic illustration of the consumable pressurization system, according to some embodiments.

FIG. 4 is a detailed schematic illustration of the consumable pressurization system 400. In many embodiments, air from the atmosphere is drawn into the consumable pressurization system 400, and the HPLC instrument generally, through an air intake 402. In other embodiments, the gas drawn into the consumable pressurization system 400 may be from a controlled source of a specific gas, such as an inert gas. The air drawn into the consumable pressurization system 400 then passes through an air filter 404 which filters out particulate matter, preventing such matter from entering the consumable pressurization system 400. The filtered air then passes through the air pump 406 and through a check valve 408 (i.e. a one-way, non-return valve) into an air reservoir 410. A first air pressure sensor 412, which in aspects can be a pressure gauge for 0.0-2.0 bar, and in other aspects may be a pressure gauge for 0.0-4.0 bar, measures the air pressure in the air reservoir 410 and communicates that information to the control electronics 306, to which the air pressure sensor 412 is electrically connected.

From the air reservoir 410, the air drawn into the consumable pressurization system 400 is directed into a pressure regulator 414. The pressure regulator 414 is controlled by a pressure regulator controller 415, which is in turn electrically connected to the control electronics 306. The pressure regulator 414 compresses the air to a specified pressure and the pressurized air is measured by a second air pressure sensor 416, which in aspects can be a pressure gauge for 0.0-1.0 bar, and which in other aspects can be a pressure gauge for 0.0-4.0 bar, which is also electrically connected to the control electronics 306. A pressure switch 418, which closes an electrical circuit upon reaching a certain pressure, is also in contact with the pressurized. Upon reaching a pressure within a specific range, the pressure switch 418 can operate to, for example, open a pressure release valve, cause an indicator to communicate a signal, allow pressurized gas into the pressurized gas channel 315, and/or trigger other operations in the bulk fluidics module 300, or in the HPLC instrument generally. The pressurized air is then directed from the consumable pressurization system 400 to the attached reagent boxes.

Figure 5A:
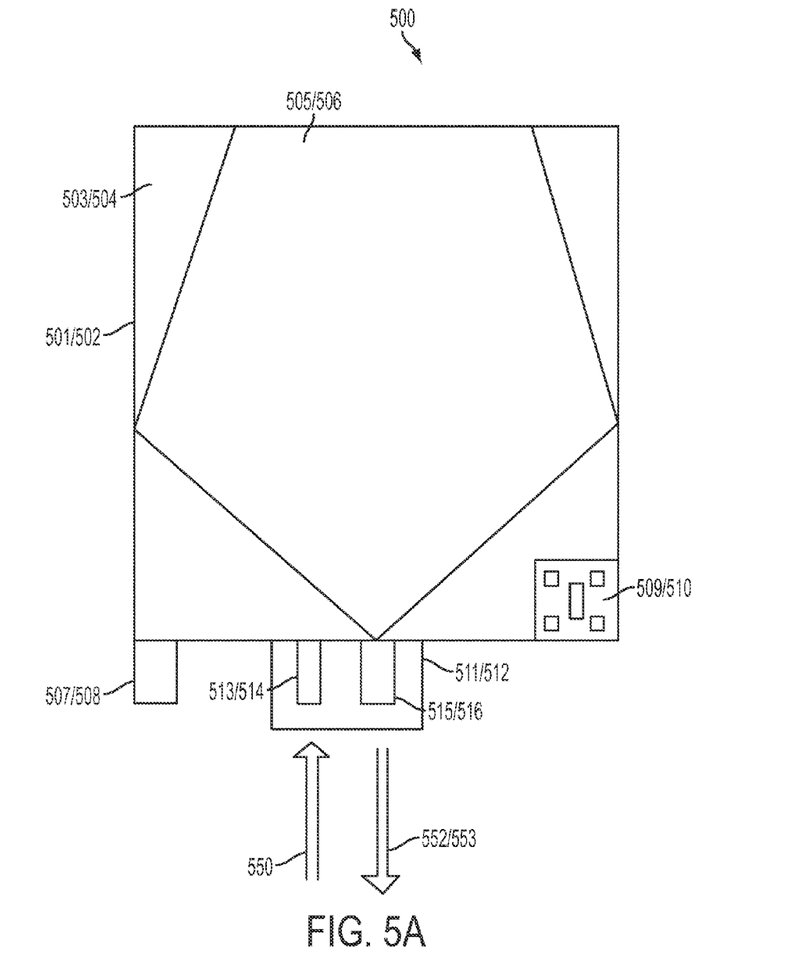
FIG. 5A is a cross-sections schematic illustration of a container assembly, according to some embodiments.

FIG. 5A is a schematic illustration of a container assembly 500, which is also referred to as a reagent box. In embodiments, a pair of reagent boxes can be used for each fluid medium to be run through the HPLC instrument. Accordingly, FIG. 5A identifies constituent parts of the illustrated reagent box with two numbers which relate to a first and second reagent box, respectively, of a pair of reagent boxes containing the same solvent. Similarly, each element can be further defined with a suffix to identify whether a reagent, buffer, diluent, or other solvent is present in the reagent box, to allow for more precise tracking of fluid and connections in the present application.

In FIG. 5A the reagent box shell 501/502 surrounds and defines an interstitial volume 503/504 that contains at least a fluid bag 505/506 (e.g. a reagent fluid bag 505a/506a or a diluent fluid bag 505*d*/506*d*) which can hold a fluid medium, such as an HPLC solvent. Pressurized gas 550 (such as air) is pumped from the consumable pressurization system 400 though a gas delivery connector or interface on the instrument (not shown) and enters the interstitial volume 503/504 through the gas interface port 513/514 in the reagent box cap 511/512. As noted in embodiments above, the reagent box cap 511/512 operates as a lid that seals the reagent box shell 501/502 and only allows for the passage of gas through the gas interface port 513/514 and the passage of fluid through the fluid interface port 515/516. In such embodiments, the lid can be detachable and re-attachable to the reagent box shell 501/502. As pressurized gas fills the interstitial volume 503/504, the pressure on the exterior surface of the fluid bag 505/506 increases, reducing the volume of the interior of the fluid bag 505/506. The coupled reagent box shell 501/502 sealed with the reagent box cap 511/512 must be able to withstand the force exerted by the pressurized gas, retaining their seal. As the volume of the fluid bag 505/506 decreases, any fluid medium inside the fluid bag 505/506 accordingly exits the fluid bag 505/506 if possible, pushed out through the fluid interface port 515/516 at a positive pressure, which is also within the reagent box cap 511/512, as fluid stream 552/553 into and through a fluid receiving connector (not shown) on the instrument. The fluid interface port 515/516 may also include a shut-off valve, such that when the fluid interface port 515/516 is not coupled to an appropriate receiving connector, fluid medium inside the fluid bag 505/506 is prevented from egressing out of the fluid bag 505/506. If fluid medium from the fluid bag 505/506 exits into the interstitial volume 503/504, the shut-off valve can also operate to prevent leakage of the fluid medium out of the container assembly 500.

In aspects, the pressurized gas 550 in the interstitial volume 503/504 can be pressurized to a pressure of about 0.5 bar, which can cause egress of fluid medium from the fluid bag 505/506 at a corresponding positive pressure. In various other aspects, the pressurized gas 550 in the interstitial volume 503/504 can be pressurized to a pressure of about 1.0 bar, about 1.5 bar, about 2.0 bar, about 2.5 bar, about 3.0 bar, about 3.5 bar, or less than about 4.0 bar. In other aspects, the pressurized gas 550 in the interstitial volume 503/504 can be pressurized to a pressure in the range of about 0.5 bar to 4.0 bar. In such aspects, the coupled reagent box shell 501/502 sealed with the reagent box cap 511/512 must be able to withstand the force exerted by the pressurized gas 550, retaining their seal. In aspects, the container assembly 500 can be a semi-rigid container, such that the walls of the container assembly 500 can bend or flex in response to the force exerted by the pressurized gas 550.

The container assembly 500 further contains a consumable tag identifier 509/510, which can be a non-transitory computer-readable memory, located within the reagent box shell 501/502, which is electrically connected to the control electronics 306 and identifies the contents of the particular reagent box connected to the HPLC instrument. The consumable tag identifier 509/510 may also include other information about the reagent box and the fluid medium contained within, such as the age of reagents or production information regarding the reagent box and/or its contents. In some embodiments, the reagent box can further include a consumable sensor 507/508, located outside of the reagent shell box 501/502, which is electrically connected to the control electronics 306 and senses the amount of consumable solvent remaining within the fluid bag 505/506. In other aspects, the consumable tag identifier 509/510 can store information regarding the amount of fluid medium remaining in the fluid bag 505/506, which can be further updated by the HPLC instrument. In such aspects, the HPLC instrument can calculate the amount of fluid medium remaining in the fluid bag 505/506 based on the amount of fluid medium sensed by the HPLC instrument entering the bulk fluidics module 300. The HPLC instrument can be informationally coupled to the consumable tag identifier 509/510, through RFID or other wireless connection, or through an electronic coupling, and update the information regarding the amount of fluid medium remaining in the fluid bag 505/506 as stored in the consumable tag identifier 509/510.

The information from either or both of the consumable tag identifier 509/510 and the consumable sensor 507/508 is relayed to the control electronics 306, and is used by the control electronics 306 to regulate gas and fluid flow through the bulk fluidics module 300. When the consumable sensor 507/508 or consumable tag identifier 509/510 communicates the amount of consumable fluid medium remaining within the fluid bag 505/506 to the control electronics 306, the control electronics 306 can further cause indicator lights (not shown) on the instrument to signal the status of the volume of fluid medium in the container assembly 500. In some embodiments, the control electronics 306 can indicate that the amount of fluid medium remaining is sufficient by triggering a green indicator light to illuminate, that the amount of fluid medium remaining is of concern by triggering a yellow indicator light to illuminate, and/or that there is no fluid medium remaining in the bottle by triggering a red indicator light source to illuminate. In aspects, any color indicator light can be used to indicate the various statuses of fluid medium in a container assembly.

Figure 5B:
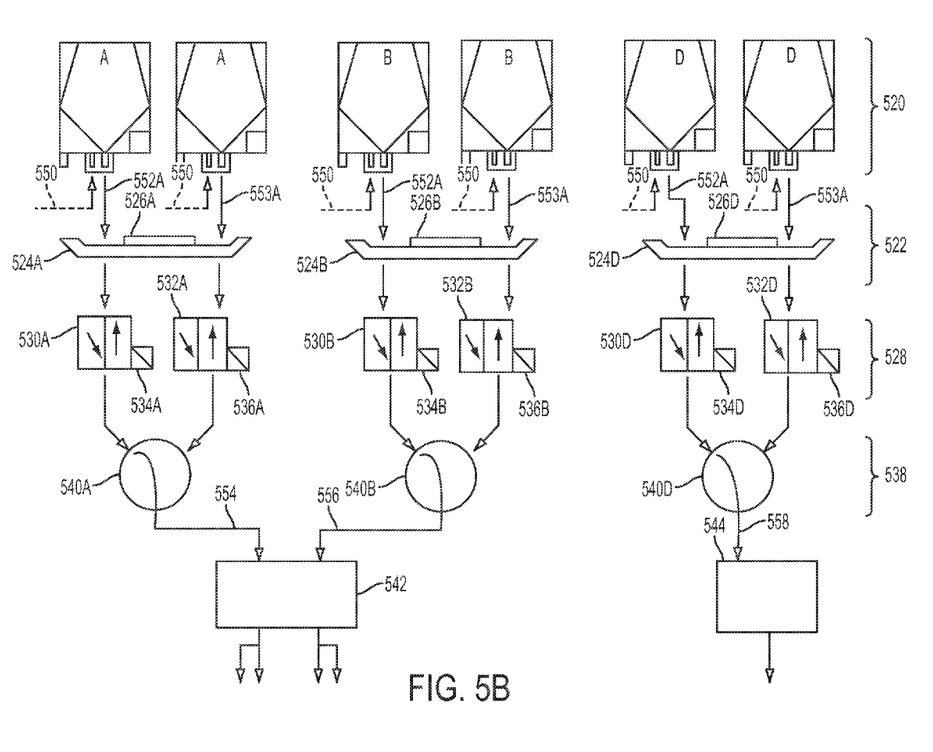
FIG. 5B is a schematic illustration of the reagent consumable region, leak detection region, reagent decompression region, fluid combiner region, buffer conditioner, and diluent conditioner, and the fluid flow through these regions, within the bulk fluidics module, according to some embodiments.

FIG. 5B is a schematic illustration of the reagent consumable region 520, leak detection region 522, reagent decompression region 528, fluid combiner region 538, buffer conditioner 542, and diluent conditioner 544, and the fluid flow through these regions, within the bulk fluidics module 300. The reagent consumable region 520 has a plurality of container assemblies 500, as illustrated in FIG. 5A, which can contain liquids such as reagents, buffers, and diluents. As described in relation to FIG. 5A, when pressurized gas 550 from the consumable pressurization system 400 enters the interstitial volume 503/504 of a reagent box, a fluid stream 552/553 egresses from the reagent box. In the illustration of FIG. 5B, fluid stream 552*a* represents a flow of reagent fluid that egresses from a first reagent box containing that reagent. Fluid stream 553*a* represents a flow of reagent fluid that egresses from a second reagent box containing the same or a different reagent as the first reagent box containing reagent. It is appreciated that in alternative embodiments, a single reagent box containing a particular reagent, or a plurality of more than two reagent boxes can be used to deliver a particular reagent or reagents into an HPLC system. Fluid stream 552*b* represents a flow of buffer fluid that egresses from a first reagent box containing that buffer. Fluid stream 553*b* represents a flow of reagent fluid that egresses from a second reagent box containing the same or a different buffer as the first reagent box containing buffer. It is appreciated that in alternative embodiments, a single reagent box containing a particular buffer, or a plurality of more than two reagent boxes can be used to deliver a particular buffer or buffers into an HPLC system. Fluid stream 552*d* represents a flow of diluent fluid that egresses from a first reagent box containing that diluent. Fluid stream 553*d* represents a flow of diluent fluid that egresses from a second reagent box containing the same or a different diluent as the first reagent box containing diluent. It is appreciated that in alternative embodiments, a single reagent box containing a particular diluent, or a plurality of more than two reagent boxes can be used to deliver a particular diluent or diluents into an HPLC system.

The fluid streams from the reagent boxes each flow into and through the leak detection region 522, wherein each type of fluid, reagent, buffer, and diluent, pass into and through a respective leak detection tray and leak detector. Specifically, reagent fluid streams 552a and 553a each pass through a region containing leak detection tray 524a, wherein any leakage of reagent fluid will be detected by leak detector 526a. Similarly, buffer fluid streams 552b and 553b each pass through a region containing leak detection tray 524b, wherein any leakage of buffer fluid will be detected by leak detector 526b. In the same manner, diluent fluid streams 552d and 553d each pass through a region containing leak detection tray 524d, wherein any leakage of diluent fluid will be detected by leak detector 526d. Each of leak detectors 526a, 526b, and 526d are electrically connected to the control electronics 306 and/or a control system external to the bulk fluidics module. When a leak is detected, an error message can be sent to the control electronics, notifying the user of the HPLC instrument of the leak, continuing operation of the HPLC instrument under sub-optimal conditions, and/or ceasing operation of the HPLC instrument. In embodiments, the leak detection region includes shut-off valves (not shown) for each connection to a bottle such that if a leak is detected, the valves prevent further fluid from the bottle identified as leaking from entering the HPLC instrument. In other embodiments, there may be more than one leak detection tray and leak detector for each type of fluid run through the bulk fluidics module.

The fluid streams continue through the leak detection region 522 and can pass through the consumable decompression region 528. The valves in the consumable decompression region 528 serve to decompress the pressure of the reagent boxes once fluids have been expelled from the reagent boxes which, due to being forced out of a fluid bag 505/506 by pressurized gas 550, may be deformed such that the walls of the external container are pressed and stuck in the region of the fluid interface due to the remaining high pressure gas in the interstitial volume of the reagent boxes. A plurality of decompression valves in the consumable decompression region 528 can be in fluid communication with the interstitial volumes 503/504 of the reagent boxes and operate to release pressurized gas from those container assemblies 500. In particular, in the embodiment illustrated by FIG. 5B, consumable decompression valve 530a, which is controlled by consumable decompression controller 534a, and is electrically connected to the control electronics 306, connects to a corresponding gas interface port of a container assembly 500 from which reagent fluid stream 552a flows. Similarly, consumable decompression valve 532a, which is controlled by reagent decompression controller 536a, and is electrically connected to the control electronics 306, connects to a corresponding gas interface port of a container assembly 500 from which reagent fluid stream 553a flows. Next, consumable decompression valve 530b, which is controlled by consumable decompression controller 534b, and is electrically connected to the control electronics 306, connects to a corresponding gas interface port of a container assembly 500 from which buffer fluid stream 552b flows. Similarly, consumable decompression valve 532a, which is controlled by consumable decompression controller 536a, and is electrically connected to the control electronics 306, connects to a corresponding gas interface port of a container assembly 500 from which buffer stream 553b flows. Finally, consumable decompression valve 530d, which is controlled by consumable decompression controller 534d, is electrically connected to the control electronics 306, connects to a corresponding gas interface port of a container assembly 500 from which diluent stream 552d flows. Similarly, consumable decompression valve 532d, which is controlled by consumable decompression controller 536d, and is electrically connected to the control electronics 306, connects to a corresponding gas interface port of a container assembly 500 from which diluent stream 553d flows. Each of the consumable decompression controllers related to the various reagent, fluid, and diluent fluid sources are specifically connected to valve control circuitry within the control electronics 306.

The fluid streams subsequently enter the fluid combiner region 538 wherein each of the reagent, buffer, and/or diluent fluid streams are combined with like fluids. Specifically, reagent fluid streams 552a and 553a both enter reagent combiner valve 540a, which mixes and combines the reagents from each fluid stream into a uniform fluid, and outputs the combined fluid as a single combined reagent stream 554. Similarly, buffer fluid streams 552b and 553b both enter fluid combiner valve 540b, which mixes and combines the buffers from each fluid stream into a uniform fluid, and outputs the combined fluid as a single combined buffer stream 556. In the same manner, diluent fluid streams 552d and 553d both enter diluent combiner valve 540a, which mixes and combines the diluent from each fluid stream into a uniform fluid, and outputs the combined fluid as a single combined diluent stream 554. Each of the reagent, fluid, and diluent combiner valves 540a, 540b, and 540d, are specifically connected to valve control circuitry within the control electronics 306.

Combined reagent stream 554 and combined buffer stream 556 are both directed from the fluid combiner region 538 into buffer conditioner 542. Both the combined reagent stream 554 and the combined buffer stream 556 are then directed from the buffer conditioner 542 to the separation module of the HPLC instrument, wherein the streams may be divided and/or recombined during the HPLC process.

Combined diluent stream 558 is directed from the fluid combiner region 538 into diluent conditioner 544. The combined diluent stream 558 is then directed from the diluent conditioner 544 to the diluent module of the HPLC instrument, wherein the stream may be divided and/or recombined during the HPLC process.

In an alternative embodiment, the roles of an interstitial volume and fluid bag in a reagent box can effectively be swapped. In such embodiments, an interstitial volume can be filled with the fluid medium to provide to an instrument, and an internal container, such as gas bag, can be collapsed and empty when the interstitial volume is filled with a fluid medium. The gas bag can be connected to a consumable pressurization system outside of the reagent box through a gas interface port and filled with a gas, such as pressurized air. The interstitial volume can be fluidity connected to a fluid interface port, which can provide a flow path for the fluid medium in the interstitial volume to enter into an instrument. As pressurized gas fills the gas bag, the volume of the interstitial volume is reduced, thereby pushing fluid medium in the interstitial volume out through the egress of the fluid interface port. In aspects of such embodiments, the gas interface port with the gas bag can be arranged on a side of the reagent box distal from the fluid interface port. In some aspects, filling the gas bag from the back of the reagent box forward can cause the fluid medium to advance toward the fluid interface port. In further aspects, the interior structure of the reagent box shell can be shaped to channel or direct fluid medium toward a fluid interface port.

Figure 6:
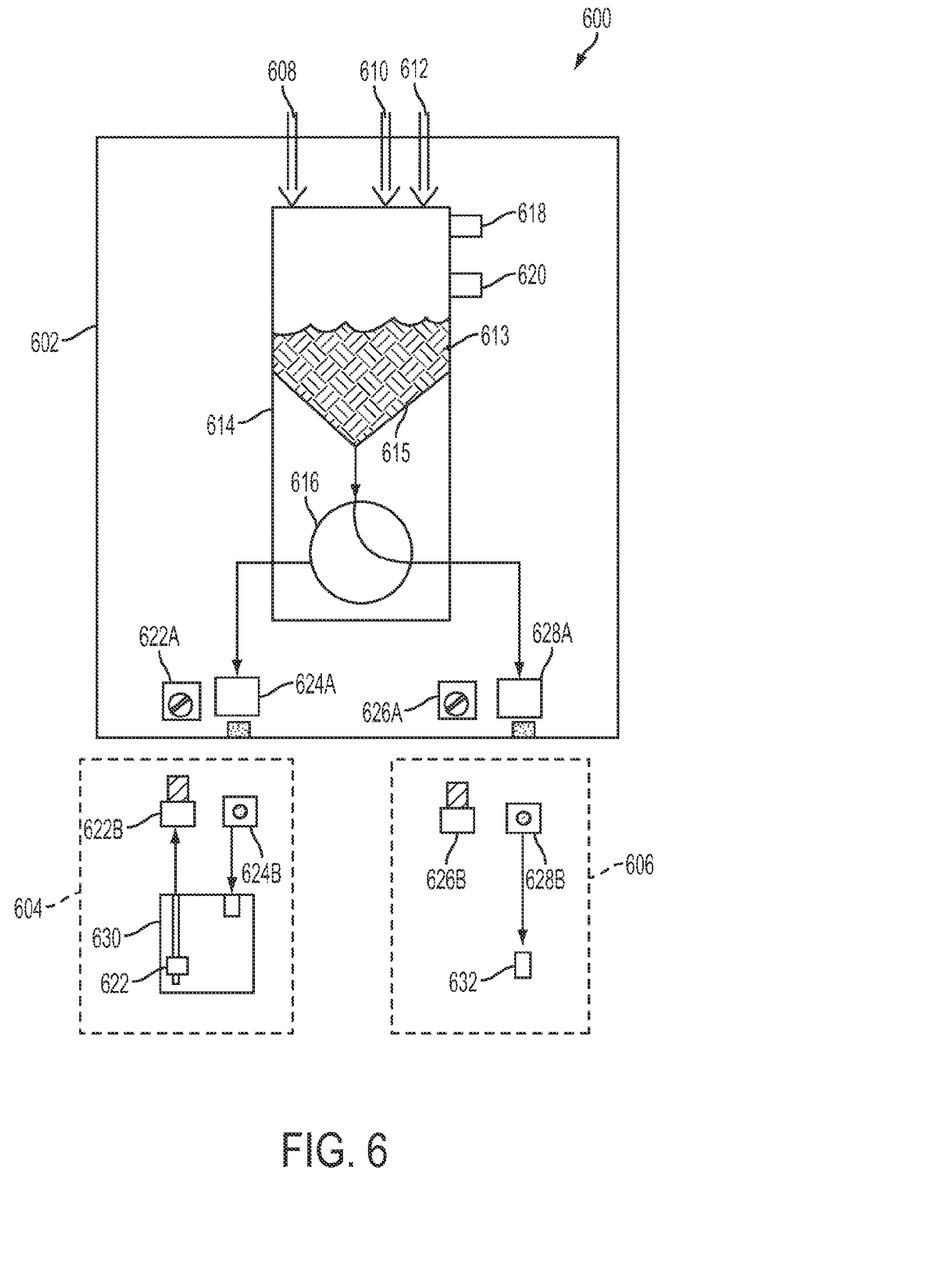
FIG. 6 is a schematic illustration of the waste handling assembly of the bulk fluidics module, according to some embodiments.

FIG. 6 is a schematic illustration of the waste handling assembly 600 of the bulk fluidics module 300. Following operational use in the HPLC instrument, waste fluids are returned to the bulk fluidics module, and specifically to the waste combiner, valve, and port subassembly 602. The waste combiner, valve, and port subassembly 602 is centered around a waste combiner and valve region 614, which is composed of a waste fluid reservoir 615 and a waste combiner valve 616. Waste diluent fluid 610 is sent to the waste fluid reservoir 615 from the HPLC dilution module. Similarly, waste reagent and buffer fluids 612 are sent to the waste fluid reservoir 615 from the HPLC separation module. The waste fluid container 615 has an air intake 608 to provide atmospheric air pressure so that the combined waste fluid 613 smoothly will move through the waste combiner, valve, and port subassembly 602. The waste combiner, valve, and port subassembly 602 further includes a waste backup sensor 618 and a back pressure regulator 620. The waste backup sensor 618, which is connected to the waste data handling circuitry of control electronics 306, detects when the combined waste fluid 613 has filled the waste fluid reservoir 615 to a maximum tolerated volume. The back pressure regulator 620 which is connected to a detection module of the HPLC instrument external to the bulk fluidics module 300, controls the amount of waste fluids 610 and 612 being provided to the waste combiner, valve, and port subassembly 602. The combined waste fluid 613 is directed from the waste fluid reservoir 615 into the waste combiner valve 616 and is further directed to either the waste container region 604 and/or the waste pipe region 606.

Combined waste fluid 613 is directed from the waste combiner valve 616 to either a waste container port 624a or a waste pipe port 628a. Combined waste fluid that is directed to waste container port 624a passes through said port, and through the waste container receiver 624b, into waste container 630. A waste container sensor is made up from a first waste container sensor component 622a within the waste combiner, valve, and port subassembly 602, a second waste container sensor component 622b external to but in contact with the waste container, and a third waste container sensor component 622c inside the waste container. The first waste container sensor component 622a is electrically connected to the waste data handling circuitry of control electronics 306, and detects when the amount fluid in the waste container 630 reaches a maximum tolerated volume. Combined waste fluid that is directed to waste pipe port 628a passes through said port, and through the waste pipe receiver 628b, into waste pipe 632 which leads outside the HPLC instrument, ideally to a proper waste disposal system. A waste pipe sensor is made up from a first waste pipe sensor component 626a within the waste combiner, valve, and port subassembly 602 and a second waste pipe sensor component 626b which is in contact with the waste pipe. The first waste pipe sensor component 626a is electrically connected to the waste data handling circuitry of control electronics 306, and monitors the flow of waste exiting the bulk fluidics module 300.

Figure 7A:
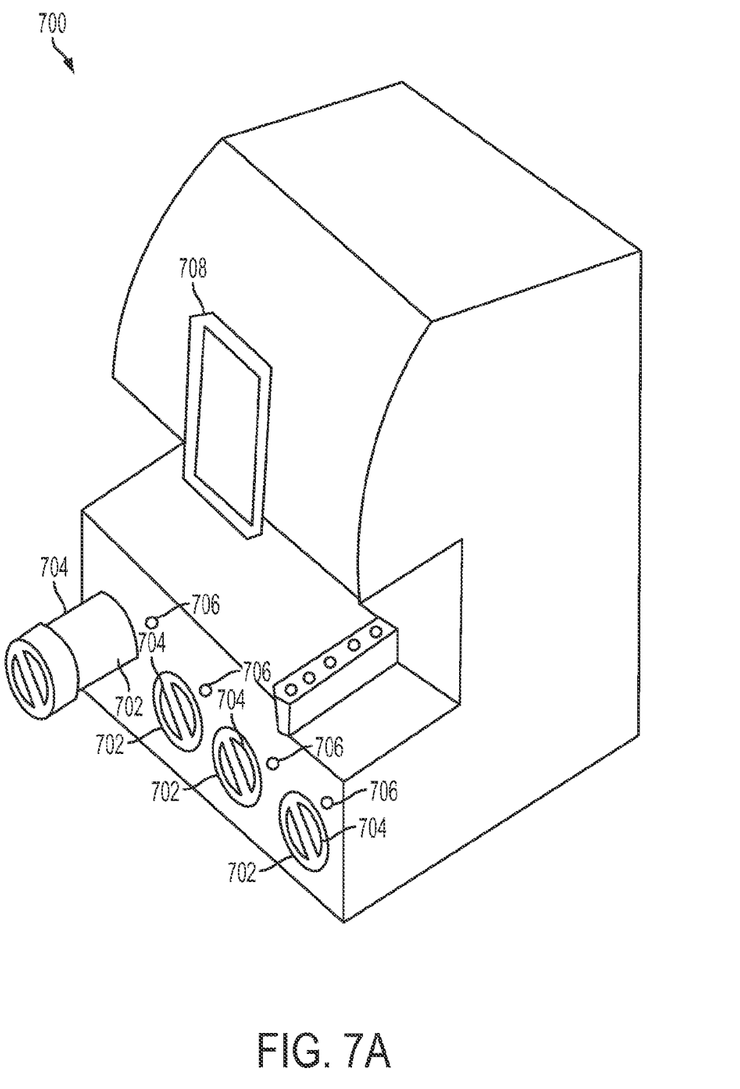
FIG. 7A is an illustration of an HPLC instrument with container assemblies, according to some embodiments.
Figure 7B:
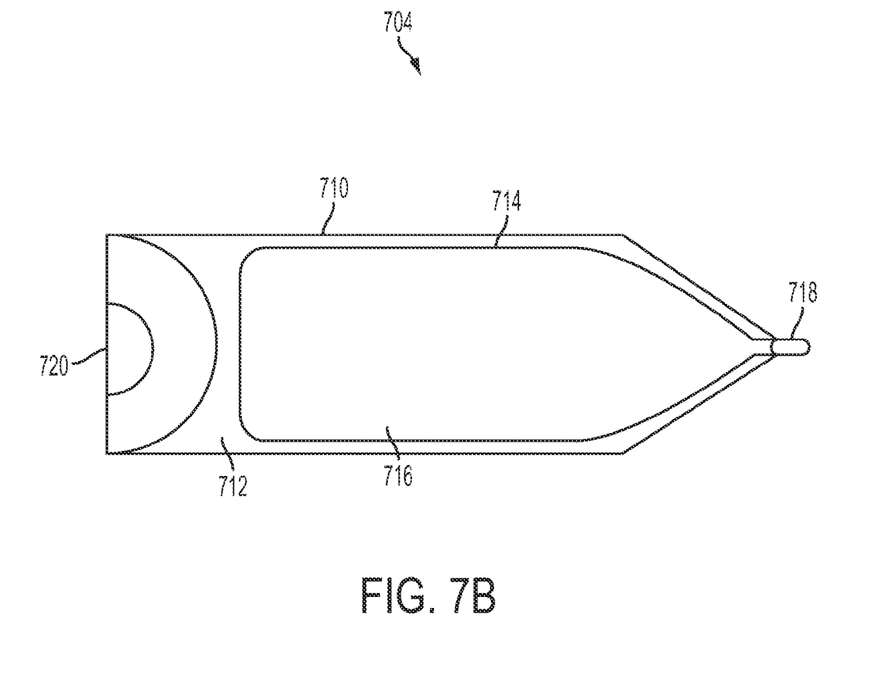
FIG. 7B is an illustration of a container assembly, according to some embodiments.

FIGS. 7A and 7B are illustrations of embodiments of the present disclosure. FIG. 7A illustrates an HPLC instrument 700 with docking stations 702 for container assemblies 704 containing fluid mediums. The HPLC instrument 700 has indicator lights 706 which can signal to a user the status of the fluid medium held within the related container assembly 704 secured within the adjacent docking station 702. For example, an indicator light 706 can provide an estimate of how much fluid medium volume is remaining in the related container assembly 704 based on the color of the indicator light. The HPLC instrument 700 can also have a user interface 708 for monitoring and interacting with the instrument. FIG. 7A further illustrates how a container assembly 704 may be horizontally mounted onto and coupled with an HPLC instrument 700. It is appreciated that in embodiments, solvents can be delivered according to operational pressures and requirements to the HPLC instrument 700 from a container assembly 704 in the illustrated horizontal or cantilevered orientation. In a horizontal or cantilever orientation, delivery of fluid medium to an instrument does not rely on gravity, thus allowing for the construction of fluidic instruments that do not require mounting fluid containers proximate to the top of the instrument. A barcode reader or QR-code reader (not shown) may be connected to the HPLC instrument 700 and be coupled with a computer system in communication with the HPLC instrument 700 for data input.

FIG. 7B is a cross-sectional illustration of a container assembly 704 that may couple with the HPLC instrument 700. The container assembly is made from an external container 710 which defines a first volume 712 and further holds an internal container 714. The internal container 714 defines a second volume 716, a volume that can hold solvent, and is fluidly sealed from the external container 710 and the first volume 712. An interface region 718 includes ports that fluidly connect the first volume 712 and the second volume 716 of the container assembly 704 to the appropriate systems of the HPLC instrument 700. The user handling region 720 is configured for a user to efficiently handle the container assembly 704. In aspects, the external container 710 can have a generally rectangular profile.

In some aspects, computerized components that can operate to control the HPLC instrument can include a processing device which can be communicatively coupled to the memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium/memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

The above description is illustrative and is not restrictive, and as it will become apparent to those skilled in the art upon review of the disclosure, that the present invention may be embodied in other specific forms without departing from the essential characteristics thereof. For example, any of the aspects described above may be combined into one or several different configurations, each having a subset of aspects. These other embodiments are intended to be included within the spirit and scope of the present invention.

The scope of the invention should, therefore, be determined not with reference to the above description, but instead should be determined with reference to the following and pending claims along with their full scope of equivalents.

What is claimed is:

1. A container assembly for holding a fluid medium, the container assembly comprising:
   an external container having a first port and a second port, the external container defining an interstitial volume fluidly connected to the first port, wherein the external container is formed of a semi-rigid material having walls configured to restorably flex, expanding when under pressure and returning to an unexpanded state when not under pressure;
   an internal container contained within the external container and being fluidly sealed from the interstitial volume, the internal container holding a fluid medium and being fluidly connected to the second port by way of a valve, wherein the internal container is formed of a flexible material;
   a sensor mechanically coupled to the external container, configured to determine a volume of the fluid medium held within the internal container; and
   a non-transitory computer-readable memory, mechanically coupled to the external container, that stores updatable information regarding the fluid medium held in the container assembly.

2. The container assembly according to claim 1, wherein the internal container is configured to channel fluid medium toward the second port.

3. The container assembly according to claim 1, wherein the valve prevents the egress of fluid medium when the container assembly is not connected to an instrument.

4. The container assembly according to claim 1, wherein the container assembly further comprises a detachable lid.

5. The container assembly according to claim 1, wherein the first and second port are configured to interface with an HPLC instrument, wherein the first port couples with a gas delivery interface on the HPLC instrument, and wherein the second port couples with a fluid medium receiving interface on the HPLC instrument.

6. The container assembly according to claim 1, wherein the non-transitory computer-readable memory is a consumable tag identifier.

7. The container assembly according to claim 1, wherein the external container is configured to contain a pressurized gas in the interstitial volume at a pressure of from about 0.5 bar to about 4.0 bar.

8. The container assembly according to claim 1, wherein the updatable information comprises the volume of the fluid medium held within the internal container as determined by the sensor.

9. The container assembly according to claim 1, wherein the updatable information comprises the age of the fluid medium held within the internal container.

10. The container assembly according to claim 1, wherein the flexible internal is a reagent fluid bag.

11. The container assembly according to claim 1, wherein the flexible internal is a diluent fluid bag.

* * * * *